United States Patent [19]
Murch et al.

[11] Patent Number: 6,046,179
[45] Date of Patent: Apr. 4, 2000

[54] COMPOSITION FOR AND TREATMENT OF INFLAMMATORY BOWEL DISEASE BY COLON ADMINISTRATION OF N-ACETYLGLUCOSAMINE

[76] Inventors: Simon Murch, c/o University Department of Paediatric Gastroenterology Royal Free Hospital, London NW3 2QG, United Kingdom; Ian W. French, 6905 Highway 9 R.R. 1, Caledon East, Ontario, Canada, L0N 1E0

[21] Appl. No.: 09/261,194

[22] Filed: Mar. 3, 1999

[51] Int. Cl.$^7$ ..................................................... A61K 31/70
[52] U.S. Cl. ............................................. 514/62; 536/1.11
[58] Field of Search ............................... 514/62; 536/1.11

[56] References Cited

U.S. PATENT DOCUMENTS

| | | | |
|---|---|---|---|
| 5,192,750 | 3/1993 | Burton et al. | 514/62 |
| 5,217,962 | 6/1993 | Burton et al. | 514/62 |
| 5,229,374 | 7/1993 | Burton et al. | 514/62 |

FOREIGN PATENT DOCUMENTS

| | | | |
|---|---|---|---|
| 1318592 | 6/1993 | Canada | 514/62 |

OTHER PUBLICATIONS

Burton, A.F. and Anderson, F.H., Decreased Incorporation of $^{14}$C–Glucosamine Relative to $^3$H–N–Acetyl Glucosamine in the Intestinal Mucosa of Patients with Inflammatory Bowel Disease. American Journal of Gastroenterology, vol. 78, No. 1, 1983.

Vantrappen, G. and Geboes, K. Glycosaminoglycans and the gut. Lancet 341: 730, 1993.

Murch, S.H. et al., Disruption of sulphated glycosaminoglycans in intestinal inflammation. Lancet 341: 711, 1993.

Murch, S.H., et al., Congenital enterocyte heparan sulphate deficiency with massive albumin loss, secretory diarrhoea, and malnutrition. Lancet 347: 1299, 1996.

Murch, S.H., Sulphation of proteoglycans and intestinal function. J. Gastroenterol. Hepatol. 10: 210, 1995.

Pender, Sylvia L.F., et al., A Major Role for Matrix Metalloproteinases in T Cell Injury in the Gut. J. Immunol. 1997; 158: 1582–1590.

*Primary Examiner*—Gary L. Kunz
*Attorney, Agent, or Firm*—Oyen Wiggs Green & Mutala

[57] ABSTRACT

This invention relates to a novel composition and a novel method of treating inflammatory bowel disease (IBD). More particularly, this invention pertains to a novel composition containing N-acetyl-glucosamine (NAG) as an active IBD treating agent and a pharmacologically suitable carrier, and a method of administering the composition to the colon to treat IBD in a person afflicted with IBD. A composition for treating inflammatory bowel disease in a patient suffering from inflammatory bowel disease comprising: (a) a therapeutic amount of N-acetyl-glucosamine; and (b) a pharmacologically acceptable carrier, adapted to be administered colonically to said patient.

28 Claims, 2 Drawing Sheets

Figure 1 at Higher Magnification

FIG. 3

Figure 2 at Higher Magnification

FIG. 4

COMPOSITION FOR AND TREATMENT OF INFLAMMATORY BOWEL DISEASE BY COLON ADMINISTRATION OF N-ACETYLGLUCOSAMINE

FIELD OF THE INVENTION

This invention relates to novel compositions and novel methods of treating inflammatory bowel disease (IBD). More particularly, this invention pertains to novel compositions containing N-acetyl-glucosamine (NAG) as an active IBD treating agent and a pharmacologically and colonically suitable carriers for the NAG, and a method of administering the compositions to the colon to treat IBD in a person afflicted with IBD.

BACKGROUND OF THE INVENTION

In general terms the "bowel" extends from the stomach to the anus and comprises the small intestine and the large intestine. The small intestine comprises three main sections, the duodenum (which is adjacent to the stomach), the jejunum (which is intermediate) and the ileum (which is distant to the stomach). The large intestine (which is termed the colon) is joined to the remote end of the ileum of the small intestine by the ileocecal valve. The large intestine (colon) comprises two main sections, the caecum (which is connected to the ileum of the small intestine), and the rectum, which is the remote part of the large intestine (colon). The remote end of the rectum is connected to the anus.

The term "inflammatory bowel disease" (IBD) is a generic expression which encompasses a number of specific bowel diseases including ulcerative colitis, chronic proctitis and Crohn's disease. These diseases may or may not overlap with one another to a certain extent. When they do, they blur the boundaries between the various types of IBD afflictions. Ulcerative colitis is a chronic, non-specific inflammatory bowel disease which involves ulcerative lesions of the colon. Chronic proctitis comprises inflammation of the colon and often the rectum. Crohn's disease appears as several types of intestinal inflammation but most often the term refers to inflammation of the terminal portion of the ileum. Synonyms of Crohn's disease are regional enteritis (the intestine) or regional iletis, although the latter is not always apt since Crohn's disease is not limited to the ileum. Crohn's disease often involves diseases, fistulas (deep sinnous passages or tracts in the colon), perianal ulcerations and narrowing of the intestinal lumen (strictures). Surgical removal of the diseased portion of the intestine (termed a colectomy, or ileectomy) is reserved for those cases which are most resistant to treatment, since about half of those treated by surgery experience a recurrence of the disease in another segment of the intestine. The most common clinical symptoms of Crohn's disease include abdominal pain, fever, anorexia, weight loss and a right lower quadrant "fullness".

Inflammatory bowel disease (IBD) can involve inflammatory disruption of vascular and matrix glycosaminoglycans (GAGs), specifically the loss of GAG's from the intestinal wall which results in fibrosis of the bowel and a loss of function (see S. H. Murch, et al., Reference 3 in Bibliography). Organ culture shows this disruption is due to the presence of matrix degrading enzymes (see S. L. Pender, et al., Reference 6 in Bibliography).

Statistics indicate that approximately 1 percent of the North American population suffer from inflammatory bowel disease (IBD) of one form or another. The annual incidence of ulcerative colitis (UC) is estimated at between six to eight cases per 100,000 population per year, with the onset of the disease occurring most frequently between the ages of 30 and 50. Since its recognition several decades ago, Crohn's Disease has increased in incidence and it is estimated to affect between twenty and seventy persons per year per 100,000 population, with 15,000 to 30,000 new cases occurring each year in the United States. By age 85, it is estimated that nearly two-thirds of the population have developed some diverticula in their colon.

A recent survey in France found an incidence of 4.9 per 100,000 for Crohn's Disease and 3.2 for ulcerative colitis. The highest age specific incidence for Crohn's Disease was 20 to 29 years, whereas for ulcerative colitis, it was between 20 and 39 years. The incidence of Crohn's Disease in France was similar to northern European studies, but the incidence of ulcerative colitis was lower.

Historically, inflammatory bowel disease (IBD) has conventionally been treated by the use of steroidal anti-inflammatory drugs such as cortisone or sulphasalazine, or antispasmodic agents such as propantheline and dicyclomine, supplemented with laxative or anti-diarrheal drugs, as well as drugs which reduce intestinal motility, depending on symptoms. More recently, 5-aminosalicylic acid (5-ASA) and related drugs, which are considered the active moiety of sulphasalazine, have been found to be effective in the treatment of inflammatory bowel disease. Their action may be related to an ability to remove irritating superoxide radicals formed in inflamed tissues. In severe, refractory disease the use of immunosuppressant drugs, such as azathioprine, may be used. In many cases, surgery to remove severely damaged intestinal tissue is required.

|  | Issue Date | Inventor |
| --- | --- | --- |
| U.S. Pat. No. |  |  |
| 5,229,374 | January 1992 | Burton and Freeman |
| 5,192,750 | March 1993 | Burton and Gislason |
| 5,217,962 | June 1993 | Burton and McLean |
| Canadian Patent No. 1,318,592 | granted June 1, 1993, | Burton |

SUMMARY OF INVENTION

The invention is directed to a composition for treating inflammatory bowel disease in a patient suffering from inflammatory bowel disease comprising: (a) a therapeutic amount of N-acetylglucosamine; and (b) a pharmacologically and bowel acceptable carrier, adapted for delivery of the N-acetylglucosamine to the bowel of said patient.

The N-acetylglucosamine can be present in the composition in an amount ranging from 0.5 gram to 5 grams. The carrier can be any medium which delivers the N-acetylglucosamine to the diseased area of the bowel. The carrier can be distilled or purified water, a foam suitable for rectal administration, a suppository base which can surround the N-acetylglucosamine, or an orally ingestible time-release substance which can withstand degradation by the gastric acids of the stomach and can release the N-acetylglucosamine in the bowel or colon. The water can be present in sufficient quantity to comprise an analeptic enema.

The foam can comprise N-acetylglucosamine, a surfactant, an adjuvant and a blowing agent. The carrier can comprise one or more substances selected from the group consisting of propylene glycol, emulsifying wax, polyoxyethylene-10-stearyl ether, ethoxylated cetyl and stearyl alcohols, stearath-10, cetyl alcohol, methyl paraben, propyl paraben, trolamine, purified water, cetyl alcohol, ethoxylated stearyl alcohol, polyoxyethylene-10-stearyl ether, methyl and propyl parabens, propylene glycol, dry ethanol amine, de-ionized water and suitable propellents.

The suppository base can be selected from the group consisting of theobroma oil, glycerinated gelatin, hydrogenated vegetable oil, polyalkyl glycol, fatty acid ester of polyalkylene glycol, coconut oil base, hydrogenated fatty acid, hydrogenated vegetable oil, monoglyceride, cocoa butter, petroleum oil, beeswax, glycerine, polyethylene glycol 600 dilaurate, hydrogenated cocoa glyceride and polyethylene glycol.

The time release substance can be selected from the group consisting of an acrylic-based resin coating, a methacrylic acid copolymer, an acrylic-based resin mixed with a suitable non-medicinal carrier such as lactose, magnesium stearate, polyethylene glycol, polyvinyl pyrolidone, or sodium starch glycolate, cellulose or ethyl cellulose, a matrix composition comprised of a hydrophilic polymer and an enteric polymer, a cellulose derivative, polyvinyl acetate phthalate, or polyvinyl acetate phthalate mixed with a plasticizer, a polysaccharide which is decomposable in the bowel, a locust bean gum or a guar gum, a film-forming polymer having hydrophilic groups, a film-forming acrylic polymer in admixture with a polysaccharide comprising from 30 to 100% by weight of at least one monomer selected from the group consisting of lower alkyl esters of acrylic acid and lower alkyl esters of methacrylic acid, a hydrocolloid gum obtained from a higher plant, and an anionic carboxylic polymer which does not dissolve at a pH below about 4 but is soluble at a pH ranging from about 4 to about 7.5.

The foam can comprise 0.5 to 5 grams of N-acetylglucosamine as the active ingredient and 20 grams of a foam containing propylene glycol, emulsifying wax, polyoxyethylene-10-stearyl ether, cetyl alcohol, methylparaben and propylparaben, trolamine, purified water and inert propellents, dichlorodifluoromethane or dichlorotetrafluoroethane.

The composition can comprises between about 0.1% by weight to about 90% by weight of N-acetylglucosamine, coated with about 5% by weight to about 29% by weight of a hydrophilic polymer, and from about 0.5% by weight to about 25% by weight of an acrylic polymer which dissolves at a pH in the range of about 5.0 to about 7.5.

The invention is also directed to a method of treating a patient suffering from inflammatory bowel disease comprising administering to the bowel of said patient a composition comprising a therapeutic amount of N-acetylglucosamine and a bowel compatible and pharmacologically acceptable carrier. The N-acetylglucosamine can be present in an amount between about 0.5 gram and 5 grams per enema.

The pharmacologically acceptable carrier can be distilled or purified water, a bowel compatible foam which can coat the colon, a suppository which can be solid at room temperature but melt at body temperature, or an orally ingestible time-release substance which can withstand degradation by the gastric acids of the stomach and release the N-acetylglucosamine in the bowel.

The enema can be administered to said patient by an enemator.

DRAWINGS

In drawings which illustrate specific embodiments of the invention, but which should not be construed as restricting the spirit or scope of the invention in any way.

DESCRIPTION

We have discovered that certain forms of inflammatory bowel disease (IBD) can be treated with good success by the administration to the afflicted area of the upper bowel or the colon of a composition containing N-acetylglucosamine (NAG) in an effective amount, and a bowel and pharmacological acceptable carrier, which can be distilled or purified water, a foam enema, a suppository, or a time-release carrier which can be ingested orally and passes largely unscathed through the stomach and releases the N-acetylglucosamine in the upper bowel or colon. The time release coating protecting the N-acetylglucosamine from attack by the gastric stomach acids can be an acrylic-based resin coating which delays release of the N-acetylglucosamine until the acrylic-based resin coated N-acetylglucosamine reaches the upper intestine or lower intestine, depending on the nature of the carrier. A suitable acrylic acid can be Eudragit S™, which is a methacrylic acid copolymer. The N-acetylglucosamine which is coated by the acrylic-based resin can be mixed with a suitable non-medicinal carrier such as lactose, magnesium stearate, polyethylene glycol, polyvinyl pyrolidone, or sodium starch glycolate. Further suitable coatings which withstand attack by stomach gastric acids can be cellulose or ethyl cellulose. The gastric acid resistant coating can also be a matrix composition which is comprised of a hydrophilic polymer and an enteric polymer. The enteric polymer is impermeable to gastric fluids of the stomach and aids in retarding release of the N-acetylglucosamine in regions of low pH, thereby allowing lower levels of N-acetylglucosamine to be employed. At the higher pH range of intestinal fluids, the hydrophilic polymer and enteric polymer dissolve and thereby release the N-acetylglucosamine in the bowel.

A specific formulation can comprise between about 0.1% by weight to about 90% by weight of the N-acetylglucosamine, coated with about 5% by weight to about 29% by weight of a hydrophilic polymer, and from about 0.5% by weight to about 25% by weight of an acrylic polymer which dissolves at a pH in the range of about 5.0 to about 7.5.

The acrylic resin should be formulated so that it withstands dissolution and attack at a pH of less than 5, but decomposes at a pH ranging from about 5 to about 8. A further suitable coating can comprise a cellulose derivative such as polyvinyl acetate phthalate, or polyvinyl acetate phthalate, mixed with a plasticizer. The latter is normally decomposable at a pH in the range pH of about 3 to about 6.

A further suitable coating can be a polysaccharide, which is decomposable in the colon, such as a locust bean gum or a guar gum, and a film-forming polymer preferably having hydrophilic groups. Such coatings are decomposed under the influence of glycosidic enzymes in the colon. The polysaccharide, which is decomposable in the colon, should contain galactose and mannose units. The film-forming acrylic polymer in admixture with the polysaccharide should comprise from about 30 to 100% by weight of at least one monomer selected from the group consisting of lower alkyl esters of acrylic acid and lower alkyl esters of methacrylic acid.

A further suitable coating used in the form of a membrane surrounding the core of the N-acetylglucosamine, and suitable non-medicinal carriers, can be a pharmaceutically acceptable, film-forming anionic carboxylic polymer which is difficult to dissolve at a low pH of less than 4, but is soluble at a higher pH ranging from about 4 to about 7.5. A further suitable gastric acid resistant coating can be a hydrocolloid gum obtained from higher plants, admixed with a suitable pharmaceutically acceptable binder.

It will be understood that in addition to selecting one or more appropriate gastric acid resistant coating(s), it is important to select an appropriate thickness of the water-insoluble coating. As will be readily understood, a thin coating will be more readily penetrated by the gastric acids than a thick coating.

The suppository can be a small solid body shaped for ready introduction into the rectum, made of the N-acetylglucosamine enclosed in a carrier substance which is hydrophilic and solid at ordinary ambient temperatures but melts at body temperature. The bases for the suppository can be theobroma oil, glycerinated gelatin, hydrogenated vegetable oil, a mixture of polyethylene glycols of various molecular weights, and/or fatty acid esters of polyethylene glycol.

The body temperature melting coatings which envelope the N-acetylglucosamine can be selected from a wide group of materials and substances such as coconut oil base, hydrogenated fatty acids, or hydrogenated vegetable oils, formulated to be solid at ambient room temperature, but which dissolve at body temperature. Other suitable coatings can be monoglycerides, cocoa butter, vegetable and petroleum oils, beeswax, glycerine, polyethylene glycol 600 dilaurate, hydrogenated cocoa glycerides, polyethylene glycol. The polymeric material should be dissolvable in body fluids, and preferably be capable of slowly releasing the N-acetylglucosamine into the rectal area while the polymeric material is dissolving in the body fluids. The film can comprise a water-soluble polymer which is bio-erodable and contains the active N-acetyl-glucosamine.

The rectal foam can typically be 0.5 to 5 grams of N-acetylglucosamine as the active ingredient in 20 g of a foam containing propylene glycol, emulsifying wax, polyoxyethylene-10-stearyl ether, cetyl alcohol, methylparaben and propylparaben, trolamine, purified water and inert propellants, dichlorodifluoromethane and dichlorotetrafluoroethane.

The foam should be hydrophilic and can be made up of propylene glycol, ethoxylated cetyl and stearyl alcohols, stearath-10, cetyl alcohol, methyl paraben, propyl paraben, trolamine and purified water, with dichlorodifluoromethane and dichlorotetrafluoroethane as propellents or blowing agents. Other foam causing carriers for the N-acetylglucosamine comprising a water miscible mucoadhesive foam base can be formulated with cetyl alcohol, ethoxylated stearyl alcohol, polyoxyethylene-10-stearyl ether, methyl and propyl parabens, propylene glycol, dry ethanol amine, de-ionized water and suitable propellents. In general, the liquid vehicle which can create the foam should include at least one surfactant, a foaming propellant such as an environmentally benign halocarbon, and an adjuvant for the active ingredients, namely, N-acetylglucosamine, which is capable of suspending or solubilizing the N-acetylglucosamine in the foam.

N-acetylglucosamine, and its precursor, glucosamine, are classified biochemically as amino sugars. Amino sugars are essential biochemical compounds formed from blood glucose by most cells of the body through a series of biochemical reactions, which were elucidated many years ago. Other amino sugars include galactosamine and mannosamine and their N-acetyl-derivatives. N-acetylglucosamine is the precursor of N-acetylgalactosamine and N-acetylmannosamine and thus, metabolically, N-acetylglucosamine plays an important role in the availability of all amino sugars which are incorporated into functional complex carbohydrates, such as glycosaminoglycans (GAG's). However, unlike galactosamine and mannosamine, N-acetylglucosamine is available in commercial quantities at reasonable cost.

N-acetylglucosamine and related amino sugars are components of a large number of high molecular weight complex polysaccharides, including the functionally important glycosaminoglycans and proteoglycans, formerly referred to as mucupolysaccharides.

Glycosaminoglycans are composed of repeating disaccharide units of N-acetylglucosamine or related amino sugars, and glucuronic or iduronic acid. Examples of glycosaminoglycans include hyaluronic acid (which is made up of repeating units of N-acetylglucosamine and glucuronic acid), chondroitin sulphate, dermatan sulphate, keratan sulphate and heparin, all of which contain either N-acetylglucosamine or the amino sugar N-acetylgalactosamine, which is synthesized from N-acetylglucosamine. Glycosaminoglycans are also present in proteoglycans, which are structures containing a number of glycosaminoglycans chains linked to a polypeptide or protein core.

N-acetylglucosamine plays an important role in the normal maintenance of cell function, including the permeability of cell membranes, the structural integrity of connective tissues such as skin and cartilage, and joint lubrication. In the intestines, glycosaminoglycans are essential to the formation of the glycocalyx of gastrointestinal cells and the mucous secreted by the intestinal goblet cells. As well, they are essential components of the extracellular fluid or "glue" which holds cells together, immunoglobulins, blood group antigens and a wide diversity of other biochemically and immunologically important substances.

The extracellular matrix, composed largely of proteoglycans containing N-acetylglucosamine, is present in the basement membrane, as well as the lamina propia, and the submucosa of the gastrointestinal tract. Proteoglycans containing N-acetylglucosamine play an important function in anchoring cells to the mucopolysaccharide layer on the epithelial cells lining the gastrointestinal tract, as well as cell repair and intestinal permeability.

Although N-acetylglucosamine is found in all cells and tissues of the body as a component of glycosaminoglycans and proteoglycans, it appears that, unlike glucose, significant concentrations of free N-acetylglucosamine or its precursor, glucosamine, are not available in the blood or intracellular fluids. Under normal conditions, the body utilizes all the available N-acetylglucosamine it produces. In disease states, such as those involving inflammatory reactions of the gastrointestinal tract (IBD), the body reserves of N-acetylglucosamine may be inadequate to support cellular repair and function at an optimal level. It has been demonstrated (see Burton et al., Bibliography Reference 1) that intestinal tissue from patients with inflammatory bowel disease preferentially incorporate N-acetylglucosamine into the bowel wall rather than glucosamine, which lends support to the need for additional N-acetylglucosamine in inflammatory bowel disease (IBD).

When N-acetylglucosamine is given to animals or humans, either intravenously or by mouth, it is quickly distributed throughout the body and incorporated within minutes into glycosaminoglycans and proteoglycans in most tissues and organs, including the intestinal tract and articular cartilage of joints. Free N-acetylglucosamine has a half-life in blood of less than ten minutes, but when incorporated into glycosaminoglycans, the N-acetylglucosamine contained in these complex molecules turns over very slowly, with a half-life measured in hours, and even days.

N-acetylglucosamine is a natural amino sugar belonging to a class of compounds that are usually very well tolerated. Mono-saccharides, and their simple derivatives, are widely used in medicine even at high doses. Even when given by intravenous administration, N-acetylglucosamine is considered to be very safe. Specifically, no mutagenicity, carcinogenicity or teratogenicity are to be expected.

Single intravenous or oral doses of N-acetylglucosamine of over 25 grams/kg body weight administered to mice or rats have resulted in no observed toxic effects. Intravenous dosing of 20 grams of N-acetylglucosamine to humans had no adverse effects, did not affect blood glucose or insulin levels, and is therefore considered safe for use by diabetics.

Studies in animals and humans have demonstrated that N-acetylglucosamine is non-toxic at doses substantially greater than those used for most medicinal purposes. Oral administration at doses of up to 3 to 6 grams/kg body weight per day for 30 days had no toxic effects, and resulted in no gross or microscopic changes in various tissues and organs. N-acetylglucosamine has been used orally, as a human nutritional supplement, at doses of up to 3 grams per day without adverse effects. For the past several months, we have administered up to 4.5 grams per day orally, or 3 grams daily rectally, to children with no adverse consequences.

In inflamed bowel tissue, it has been demonstrated by Burton et al. (see Reference 1 in Bibliography) that there is a preferential incorporation of N-acetylglucosamine over glucosamine. This may be the result of a biochemical deficiency in the process by which glucosamine is converted to N-acetylglucosamine in the intestinal cells. The acetylation step in the conversion of glucosamine to N-acetylglucosamine may be deficient. This would result in a reduction of the protective glycocalyx or proteoglycans covering the intestinal cells, as well as a decrease in mucus production and the slowing of diseased tissue repair. As a result of the loss of these protective components, the intestinal wall would be more susceptible to damage, inflammation and ulceration. While we do not wish to be bound adversely by any theories, it appears that N-acetylglucosamine is more readily absorbed into cells as a result of its passive diffusion across cell membranes, as compared to the apparent active transport mechanism (a complex, energy requiring system) required for the intracellular distribution of glucosamine. We have observed that in inflammatory bowel disease, there is a loss of N-acetylglucosamine-containing glycosaminoglycans from the intestinal wall which results in the bowel wall becoming abnormally thick, or fibrotic. When this occurs, the permeability and function of the gut is impaired.

Although symptoms of ulcerative colitis and Crohn's Disease are similar and are often hard to differentiate, a gross pathological difference is that Crohn's Disease is an inflammatory condition in which inflammation and ulcerations may be distributed along any part of the entire gut. In Crohn's Disease, fibrosis of the gut may be extensive causing luminal narrowing, resulting in bowel obstruction. Both ulcerative colitis and Crohn's Disease can become serious and may require intensive drug therapy or surgery. Patients with inflammatory bowel disease exhibit high cellular turnover in the gut wall, often leading to ulceration or fistulas. The chronic nature of these inflammatory conditions, as well as the tendency to affect younger people with the peak incidence of ulcerative colitis occurring between 15 and 30 years of age, makes inflammatory bowel disease a serious medical problem. Onset of the disease most often occurs during adolescence or early adulthood.

Diverticulitis is a more common, but less severe gastrointestinal condition that is often categorized with inflammatory bowel disease. This disorder is an inflammation of one or more diverticular, which are sac-like outpouchings of the colon wall that occur at weak points. In diverticulitis, the cell wall of the colon is primarily affected and the symptoms range from relatively minor discomfort to painful perforation of the intestinal lining. Diet has been implicated as a causative or contributing factor to the development of diverticulitis, which is also associated with increasing age, being uncommon in individuals under the age of 35. The disorder is progressive, developing from mild symptoms to painful inflammation. Early stages of diverticulitis may respond to a modified diet, but later stages require medication or surgery.

In inflammatory bowel disease, including Crohn's Disease, there is a significant loss of glycosaminoglycans (GAG's) from the intestinal wall, providing further evidence of the involvement of glycosaminoglycans in the pathology of inflammatory bowel disease. We do not wish to be bound by any incorrect theories. However, the following is offered as a possible explanation of the foundation for the invention. The finding of loss of GAG's from the bowel well supports the rationale for the beneficial effects of N-acetylglucosamine in the treatment of inflammatory bowel disease, since N-acetylglucosamine would provide the necessary substrate or amino sugar components needed to replace, or prevent the loss of glycosaminoglycans. The normal loss and turnover of intestinal cells is about half a million cells per minute. This increases by as much as three to five times in inflammatory bowel disease. This may explain the need for additional amino sugars in order to support cellular regeneration since the systemic pool of free amino sugars is very limited. If the loss of epithelial cells in the gut exceeds the rate of production, it follows that the integrity of the mucosa would be compromised. To further support the concept of N-acetylglucosamine preventing or replacing the bowel wall glycosaminoglycans in inflammatory bowel disease, we have observed that N-acetylglucosamine has a significant effect in stimulating the synthesis of hyaluronic acid when applied to the intestinal epithelium or to human mesothelial cells isolated from the intestinal peritoneum.

EXAMPLE 1

Preliminary research conducted at The University of British Columbia has demonstrated that N-acetylglucosamine is a preferential precursor in the synthesis of the constituent glycosaminoglycans and proteoglycans in the inflamed and damaged tissues occurring in inflammatory bowel disease. This research suggests that the oral administration of N-acetylglucosamine supplements the body's supply of the essential amino sugars when under the stress of excessive tissue breakdown and loss.

EXAMPLE 2

The effect of N-acetylglucosamine on digestive tissue has also been demonstrated in a confidential animal model of inflammatory bowel disease carried out at the Department of Biology at Queen's University, Kingston, Ontario. Trinitrobenzenesulfonic acid and alcohol instilled intrarectally in rats caused a chronic inflammatory bowel reaction with ulcers, bowel wall fibrosis or thickening, and pathological and histological changes similar to those seen in ulcerative colitis. It was found that a single intrarectal instillation of N-acetylglucosamine (NAG), prior to challenge with trinitrobenzenesulfonic acid (TNB), had a significant, dose-related effect in reducing the number and severity of the ulcerative lesions, as well as reducing bowel wall thickening (see Table 1 below).

TABLE 1

Bowel Wall Fibrosis in
Trinitrobenzenesulfonic Acid (TNB)-Ethanol Treated Rats
Colon Fibrosis (weight (gm) of 8 cm of colon)

| Intrarectal Administration | Mean ± sum |
|---|---|
| Control (20 mg TNB* in 0.25 mL ethanol) | 2.301 ± 0.222 |
| 25 mg NAG/kg Bwt 1 hr. before TNB/EtHO | 1.669 ± 0.142 |
| 50 mg NAG/kg Bwt 1 hr. before TNB/EtHO | 1.339 ± 0.155* |
| 100 mg NAG/kg Bwt 1 hr. before TNB/EtHO | 1.150 ± 0.068* |

*Statistically significant different from control group

EXAMPLE 3

Additional evidence that N-acetylglucosamine stimulates glycosaminoglycans synthesis was observed in an ex vivo rat gastric model, in which the blood supply to the stomach is maintained but the stomach is opened and placed in a plastic chamber, allowing drugs to be placed on the inside, mucosal surface. When N-acetylglucosamine was placed on the mucosal surface of the stomach, copious quantities of mucus were observed being released from the goblet cells of the stomach. On the basis of this observation, additional experiments were carried out in which it was found that in the presence of ethanol (which is a gastric irritant), N-acetylglucosamine, but not glucosamine, caused a significant reduction in the potential difference between the mucosal and serosal surfaces. This phenomenon may be a result of N-acetylglucosamine stimulating the synthesis of sulphated glycosaminoglycans. The effect of N-acetylglucosamine in stimulating mucus release by the stomach may explain the anecdotal clinical claims that N-acetylglucosamine is effective in the treatment of non-erosive gastritis.

In inflammatory bowel disease, there is also a disruption of vascular and matrix glycosaminoglycans. Organ culture shows this to be due to matrix degrading enzymes. N-acetylglucosamine is a substrate for glycosaminoglycans production, but in addition to its role as a fuel in fibroblast matrix synthesis, there is evidence that N-acetylglucosamine can act intracellularly as an antagonist of O-phosphorylation and may thereby regulate many inflammatory pathways.

EXAMPLES 4 to 23

Clinical Evidence of the Effect of N-acetylglucosamine in Inflammatory Bowel Disease Research has been conducted at the Royal Free Hospital in London, U.K., and it was noted that there is a loss of glycosaminoglycans from the intestinal wall in patients with inflammatory bowel disease, which is associated with bowel wall thickening or fibrosis. Ethics approval was obtained to treat children with serious, intractable upper or lower inflammatory bowel disease with oral N-acetylglucosamine. To date, over twenty children have been treated with N-acetylglucosamine at doses of up to 12 grams a day. The children were generally resistant to other therapy, including such toxic drugs as azathioprine and intravenous steroids, and therefore there were minimal expectations that N-acetylglucosamine would provide a significant clinical benefit. Of the initial six patients treated, three with upper inflammatory bowel disease have responded well, with one child doing better than on any previous therapy. Three children with lower inflammatory bowel disease did not demonstrate significant therapeutic response with oral N-acetylglucosamine. This is not unexpected since only a small fraction of each oral dose would be expected to reach the diseased tissue in the lower bowel.

In order to expose the inflamed colon to a higher concentration of N-acetylglucosamine, patients with lower inflammatory bowel disease have been administered N-acetylglucosamine by rectal enema at a dose of 1 to 2 grams three times a day. The initial three patients had symptomatic clinical improvement within forty-eight hours of initiating therapy. Pre- and post-biopsies of the colon of several children indicated that, after six weeks of rectal N-acetylglucosamine therapy, there was a significant improvement in the histopathology of the bowel wall.

Figure 1:
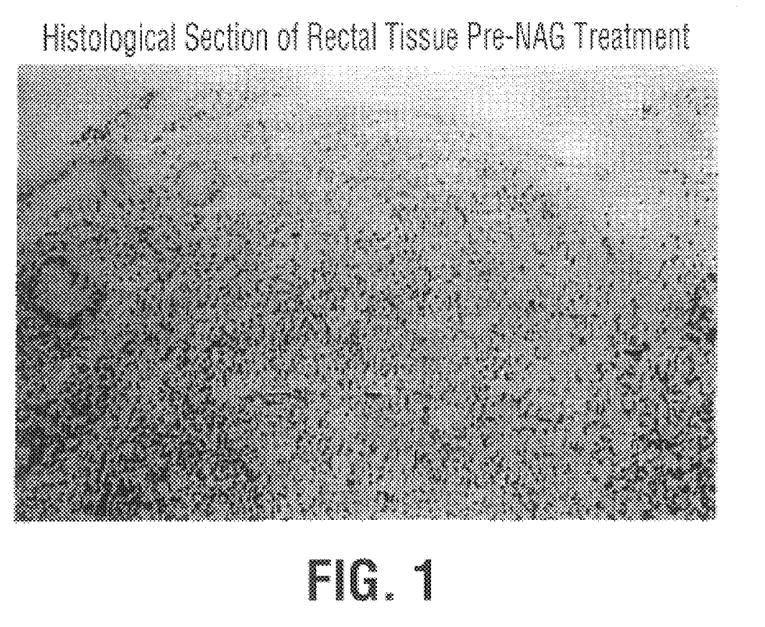
FIG. 1 depicts a histological section of rectal tissue prior to treatment with N-acetylglucosamine.
Figure 2:
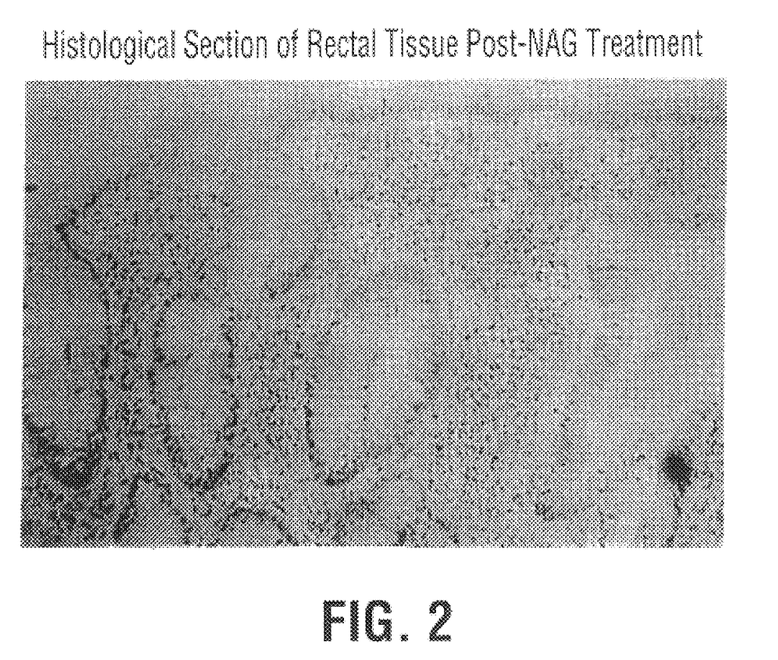
FIG. 2 depicts a histological section of rectal tissue after treatment with N-acetylglucosamine.
Figure 3:
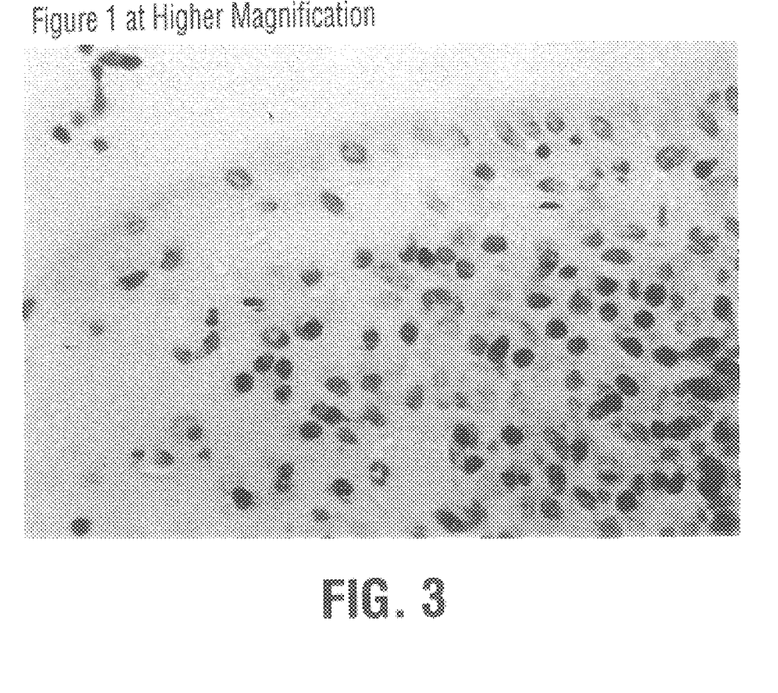
FIG. 3 depicts a higher magnification of the histological section depicted in FIG. 1.
Figure 4:
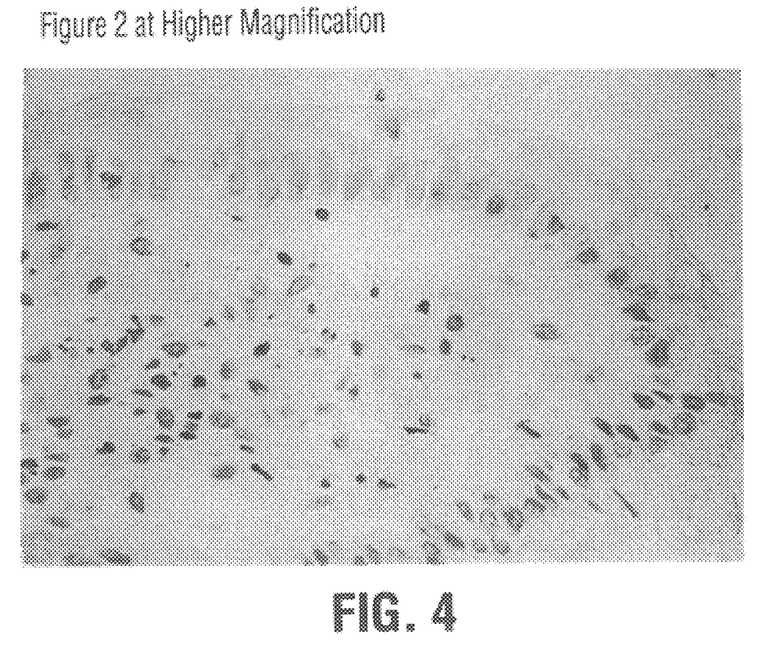
FIG. 4 depicts a higher magnification of the histological section depicted in FIG. 2.

A representative example of this effect is shown in FIGS. 1 and 2. FIG. 1 is a section from the pre-N-acetylglucosamine treatment biopsy, and clearly demonstrates that prior to N-acetyl-glucosamine therapy, an atrophic epithelium with heavy inflammatory infiltrate and fibrosis was present. Pre-treatment there was an almost complete void of villi and the epithelial membrane was virtually absent. The post-N-acetylglucosamine treatment biopsy (FIG. 2) indicates the presence of significantly less inflammatory infiltrate, as well as an increase in the number of villi and an almost normal epithelial membrane. FIGS. 3 and 4 are pictures of the same biopsies depicted in FIGS. 1 and 2, but at a higher magnification. An important finding is the significant reduction in the fibrosis of the bowel wall.

Rectal administration of NAG (1.5–2 g bd), as a single therapy, to nine children with therapy-resistant proctitis of distal colitis induced clinical remission in four of those children, improvement in three of the children, and no effect in two of the children. Biopsies before and after treatment have shown histological improvement in four of five children, with a striking increase in glycosaminoglycan (GAG) density in the bowels of such children (which has not seen with other treatments) and intraepithelial wheat germ agglutin (WGA) staining. Epithelial morphology was particularly improved. Oral NAG (1–1.5 g bds) was added to the treatment of eleven children with severe small intestinal and colonic disease, including seven with critical strictures. Eight of the eleven children showed improvement, while three did not and required surgical resection. Six of the seven children with treatment-resistant strictures showed marked resolution of symptoms. Endoscopic or radiological assessment confirmed substantial improvement in four of the six children. GAG and WGA staining was again denser in the NAG treated children than in children treated with steroids or enteral nutrition.

This first uncontrolled trial suggests that NAG is of therapeutic efficacy in resistant IBD, with a mode of action distinct from conventional therapies. Its lack of known adverse effects makes it particularly suitable for therapeutic use.

Commencing on or about April, 1996, an extensive study of the use of prescribed dosages of N-acetylglucosamine (NAG) on paediatric patients of the Royal Free Hospital suffering from inflammatory bowel disease has been conducted. Since commencing the tests with NAG on or about April, 1996, extensive case histories on those children tested with NAG have been compiled. Details of biopsies and other relevant information taken from such case histories are reproduced in summary form as follows. The patient in each case is identified by his or her initials.

Rectal Administration in Ulcerative Colitis (UC) and Chronic Proctitis Following Colectomy (Removal of Part of Colon Leaving Rectal Stump) and Ileostomy (Artificial Opening in Ileum to Evacuate Feces through Abdomen)

UC with previous subtotal colectomy, ileostomy and mucous fistula, now with chronic proctitis (presumed due to defunction and underlying UC).

1. ZY. Intractable proctitis within rectal stump, failed previously on metronidazole and corticosteroids. Commenced NAG December 1996, dose 2 grams once daily p.r. Clinical response within 2 days, with cessation of blood loss. Post-treatment biopsy at 2 months showed significant improvement, particularly in epithelial morphology and integrity, with 30–50% reduction in inflammatory infiltrate. Has been treated with NAG continually since, with only minimal symptoms.

2. SG. Clinical problem, inflammation of ileo-anal pouch, with additional problems due to failure of pouch growth with age (thus symptoms only partly due to inflammation). Had failed to respond previously to cyclosporine, interferon-α, corticosteroids, long-chain fatty acid enemas, metronidazole, codeine phosphate. Commenced NAG March 1997, dose 2 grams once daily pr (unhappy with twice daily enema regime). Modest clinical response, but histology after 1 month showed definite improvement compared to pre-treatment biopsy, with overall reduction in histological Pouchitis Index from 9/12 to 6/12. Continues with rectal NAG in view of histological response. Has subsequently achieved complete clinical remission with NAG in combination with antibiotics (metron, diazole and ciprofloxacin).

3. SB. Severe long-term inflammation of rectal stump, unresponsive to corticosteroid enemas, metronidazole and ciprofloxacin. Commenced NAG enemas April, 1997, dose 1 gram twice daily rectally. Only minor clinical improvement reported at 2 months, but significant histological response compared to pre-treatment biopsy. In this case, the inflammatory infiltrate was significantly reduced, while epithelial changes were less marked.

4. MS. Intractable inflammation of rectal stump, unresponsive to cyclosporine, corticosteroids and antidiarrhoeals. Commenced NAG enemas (1 gram three times daily) initially in October, 1996, with substantial improvement. Biopsies were not performed at that time. The enemas were stopped because of good clinical progress in December, 1996, and his symptoms gradually returned. He was recommenced on NAG enemas in June, 1997 (1 gram twice daily) after pre-treatment biopsy.

5. LE. (possible diagnosis Crohn's, but with similar post-colectomy rectal stump inflammation, unresponsive to corticosteroids and cyclosporine). Commenced NAG enemas (1.5 grams twice daily) June, 1997, following pre-treatment biopsy. Follow-up clinical assessment and biopsies in August, 1997 have shown significant improvement.

6. SE-K. Severe persistent inflammation of rectal stump, resistant to topical and systemic steroids, metronidazole, ciprofloxacin. Commenced on rectal NAG (1.5 grams twice daily) in June, 1997. Pre-treatment biopsy showed anal mucosa thus post-treatment biopsy will be difficult to interpret. However the clinical response has been prompt and marked, and she has shown complete resolution of bleeding and discharge.

7. RM. Persistent inflammation of rectal stump, with severe perianal inflammation. Treatment (1 gram twice daily) discontinued at child's request after brief period because of pain on inserting enema catheter.

Rectal Administration in Distal Intestinal Disease (Without Surgery Involving Removal of Part of Colon Leaving Rectal Stump (Colectomy)

8. MI. Chronic distal proctitis, of indeterminate histology, resistant to corticosteroids and ciprofloxacin. The proctitis was limited to the first 5 cm of the colon only, and did not involve the rectum. NAG enemas (1.5 grams bd) commenced February, 1997, discontinued after 2 months without effect.

9. SE. Severe ulcerative peri colitis, almost requiring emergency surgery in July, 1996. During this episode, she had received intravenous azathioprine, intravenous heparin, intravenous corticosteroids and was additionally commenced on NAG during the convalescent phase. This was at a dose of 1 g three times daily orally and 1 g twice daily rectally. She has subsequently been maintained on azathioprine, variable corticosteroid doses and aminosalicylates. She has shown an extremely good clinical response, in the circumstances of her severe disease, which we would normally have treated surgically, but in this case it was avoided. Although it is impossible to determine the individual contribution of NAG, it is very noticeable that her rectal biopsies showed signs of relatively improved histology, which were not detectable before the NAG enemas were commenced. She is currently well and continues oral NAG, azathioprine and low dose heparin.

Crohn's Disease (With or Without Surgery)

10. AT. This boy has Crohn's disease and a tight anal stricture, which due to the boy's growth has required regular surgical dilatation for the last three years. He is maintained on a low dose oral prednisolone and aminosalicylates for his disease, and commenced NAG enemas (1 g twice daily) in December, 1996. Since commencement of NAG he has shown marked clinical improvement, and subsequent examination under anaesthesia in March, 1997 showed clear improvement in his anal stricture, with substantially less dilatation needed. Mucosal inflammation also was noted to have decreased. He subsequently remained entirely asymptomatic.

11. HS. A girl with long-standing Crohn's disease, previous hemicolectomy and surgery for multiple strictures. Previously treated with enteral nutrition, corticosteroids, azathioprine, cyclosporin and aminosalicylates. Previous barium examinations had shown extensive stricturing, and she had become grossly cushingoid because of steroid treatment. NAG was commenced in July, 1996 (1 g three times daily by mouth), and this was associated with clear improvement in stricture related symptoms and reduction in inflammatory markers. She has had one minor relapse in January, 1997, but has subsequently been well. Follow up barium examination in April, 1997 was normal.

12. GC. A boy with severe left-sided Crohn's colitis, (which is clinically notorious as a variant of the disease virtually resistant to treatment) resistant to enteral nutrition, azathioprine and corticosteroids. In addition, he had an associated inflammatory anal stricture. He was commenced on NAG (1 g three times daily by mouth and 500 mg twice daily rectally) in April, 1996, in addition to his intensive therapeutic regime. Although subsequent endoscopy did show evidence of rectal sparing, that had not been evident previously, his symptoms remained intractable and he underwent subtotal colectomy in February, 1997.

13. GN. A boy with a similar history to GC (above) of intractable left sided Crohn's colitis. He had failed to respond to corticosteroids, aminosalicylates, enteral nutrition and azathioprine. He was commenced on NAG (1 g three times daily by mouth) in April 1996. He had minimal response to this, and underwent subtotal colectomy in March, 1997.

14. LC. The third patient with severe left sided Crohn's colitis. She has been managed on enteral nutrition, aminosalicylates, corticosteroids and azathioprine. Four months after commencement on azathioprine, she remained severely unwell with persistent rectal bleeding, severe anaemia and marked increase in inflammatory markers. She was commenced on NAG in February, 1997 (1 g three times daily by mouth) in addition to azathioprine and steroids. She showed marked clinical improvement within two weeks of commencing NAG, and has subsequently gone into complete remission. The only complicating factor in interpreting this case is that azathioprine may show a delayed onset of efficacy, but the temporal association of improvement with NAG was very striking, and she has avoided the colectomy that we had thought previously would be inevitable. There was recently a NAG supply problem and her symptoms have recurred.

15. DB. This boy has relentlessly severe Crohn's disease affecting the terminal ileum, with stricture. He had failed on treatment with corticosteroids, enteral nutrition, azathioprine and aminosalicylates. He was commenced on NAG (1 g twice daily by mouth) in April, 1996. He showed limited clinical response, and underwent hemicolectomy in June, 1996. The severity of his disease was shown by a rapid early relapse and currently he pursues a relentless course of the disease.

16. RP. This girl has a stricturing form of Crohn's disease, and had undergone previous removal of two small intestinal strictures, when the surgeons noted multiple other strictures throughout the small intestine (bowel) (January, 1995). She had been managed with enteral nutrition and aminosalicylates, plus intermittent corticosteroids. In view of severe stricture-related symptoms, confirmed by barium follow through in March, 1996, when she had multiple small intestinal strictures, she was commenced on NAG in March, 1996, (initial dose 1 g three times daily, increased to 2 g three times daily in August, 1996). Barium assessment showed reduction in stricturing after one month of NAG treatment, associated with very marked clinical improvement. Subsequent barium examinations in September and December, 1996 showed no evidence of stricture. Thus we have radiological and clinical evidence of NAG improvement in stricturing small intestinal Crohn's disease.

17. EH. This girl has a long stricture of her terminal ileum, associated with long-standing Crohn's disease. This was confirmed by barium follow through in December, 1996 when there was marked pre-synoptic dilatation and she was complaining of obstructive pain after taking solids. She had been managed with enteral nutrition, aminosalicylates and steroids. She was commenced on NAG (1 g three times daily by mouth) in November, 1996 in addition to her current treatment. Within three to four weeks she became asymptomatic and was able to eat an unrestricted diet. She remains asymptomatic and has weaned off steroids. Follow up barium examination in June, 1997 showed decrease in the stricturing, although she still has radiologically a significant stricture. Undoubtedly, without the NAG treatment she would have required hemicolectomy and removal of her stricture as this was at a critical level in November, 1996. At this time, we are uncertain whether she will entirely avoid surgery, but she certainly will remain on NAG in the long term because of its obvious benefits to her.

18. ML. This boy has stricturing Crohn's disease, with history of a previous hemicolectomy, resection of strictures, and then the development of gastric outlet obstruction due to stricturing duodenal disease. He underwent endoscopic dilatation in May, 1996 and was commenced on NAG at that time (1 g twice daily). His additional treatment was based on enteral nutrition. Salazopyrine and azathioprine in addition to Omeprazole (a steroid). He underwent re-dilatation in July, 1996, when the stricture had improved, and this was confirmed by barium swallow in August, 1996. Repeat endoscopy in March, 1997 showed significant improvement, with almost no evidence of residual stricture. However he was readmitted with recurrence of his stricture, and has now undergone surgery for this. He has continued with the NAG treatment in the meantime, in addition to his other treatment. Thus the early apparent improvement in stricturing was not maintained but there is a benefit because he has been taken off Omeprazole in the meantime.

19. IJ. This boy also has multiple strictures of his small intestine, with very aggressive Crohn's disease. He has previously failed on enteral nutrition, azathioprine and high dose corticosteroids and has also previously undergone hemicolectomy. He was demonstrated to have multiple critical strictures throughout the small bowel (small intestine), which represents a major therapeutic problem. He was commenced on NAG (1.5 g three times daily by mouth) in February, 1997, in addition to continuing his previous treatment with azathioprine and enteral nutrition. He has shown gradual improvement, both in terms of his stricture related symptoms and his inflammatory indices. An early barium examination in March, 1997 showed no significant improvement in the strictures after one month on NAG. A follow up barium study will probably be performed in the autumn.

20. NBL. This girl has stricturing small bowel Crohn's disease, with a long terminal ileal stricture with pre-synoptic dilatation. She has been managed with enteral nutrition and aminosalicylates previously. She was commenced on NAG (1.5 g three times daily) in April, 1997, in association with enteral nutrition. She is significantly improved clinically, with no current stricture associated symptoms when reviewed in June, 1997. We plan to perform a follow up barium study.

Overall Assessment

The foregoing evidence confirms that NAG has definite therapeutic effect in the treatment of inflammatory bowel disease. There are certain clear areas where NAG appears to out-perform conventional treatments. NAG clearly shows efficacy by rectal administration in the defunctioning colitis following subtotal colectomy. Several of the NAG treated children reviewed have shown very prompt clinical improvement. Follow up histological examination in three NAG treated children shows definite improvement. In addition, the children who had more extensive colitis developed evidence of rectal sparing which had not been there previously.

NAG also appears to be of benefit in the stricturing variant of inflammatory bowel disease (IBD), particularly in upper small intestinal strictures. Only a single long term treatment failure occurred in the last month because of a temporary NAG supply problem, and all other NAG treated children suffering from small intestinal strictures have shown benefit. Certainly NAG has been instrumental in avoiding early stricture surgery in two children, who had critical strictures before commencing NAG treatment and they are currently asymptomatic.

The cases where NAG appears to be less successful have been in the treatment of terminal ileal and upper colonic disease, when the NAG was given by mouth. In contrast, rectal treatment by NAG has shown marked improvement. The latter success is probably due to the fact that rectally administered NAG does not have to pass through the digestive process of the gut. It follows that administering NAG with a suitable carrier that can deliver the NAG to the IBD area will be successful in treating the IBD. Suitable carriers for rectal administration can be distilled or purified water, a foam suitable for rectal administration, or a suppository. A suitable carrier for oral administration is a coating, or a double coating, in which the NAG is protected, the coating or double coating withstanding acidic and enzymatic degradation by the stomach and small intestine, until the afflicted IBD area is reached. Then the coating is digested and the NAG is delivered unscathed to the afflicted area.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

BIBLIOGRAPHY

1. Burton, A. F. and Anderson, F. H. Decreased Incorporation of $^{14}$C-Glucosamine Relative to $^3$H-N-Acetyl Glucosamine in the Intestinal Mucosa of Patients with Inflammatory Bowel Disease. J. Biol. Chem. 78: 19, 1983.

2. Vantrappen, G. and Geboes, K. Glycosaminoglycans and the gut. Lancet 341: 730, 1993.

3. Murch, S. H. Disruption of sulphated glycosaminoglycans in intestinal inflammation. Lancet 341: 711, 1993.

4. Murch, S. H., et al. Congenital enterocyte heparan sulphate deficiency with massive albumin loss, secretory diarrhoea, and malnutrition. Lancet 347: 1299, 1996.

5. Murch, S. H. Sulphation of proteoglycans and intestinal function. J. Gastroenterol. Hepatol 10: 210, 1995.

6. Pender, S. L., Gut 1996; 39: 284–290, J. Immunol. 1997; 158: 1582–1590.

What is claimed is:

1. A composition for treating inflammatory bowel disease in a patient suffering from inflammatory bowel disease comprising:
    (a) a therapeutic amount of N-acetylglucosamine; and
    (b) a pharmacologically and bowel compatible carrier, adapted for delivery of the N-acetylglucosamine to the bowel of said patient, said carrier being selected from the group consisting of:
       (i) a foam suitable for rectal administration;
       (ii) a suppository base which surrounds the N-acetylglucosamine; and
       (iii) an orally ingestible time-release substance which withstands degradation by the gastric acids of the stomach and releases the N-acetylglucosamine in the bowel.

2. A composition as claimed in claim 1 wherein the N-acetylglucosamine is present in the composition in an amount ranging from 0.5 gram to 5 grams.

3. A composition as claimed in claim 1 wherein the carrier is a foam suitable for rectal administration.

4. A composition as claimed in claim 2 wherein the carrier is a foam suitable for rectal administration.

5. A composition as claimed in claim 1 wherein the carrier is a suppository base which surrounds the N-acetylglucosamine.

6. A composition as claimed in claim 2 wherein the carrier is a suppository base which surrounds the N-acetylglucosamine.

7. A composition as claimed in claim 1 wherein the carrier is an orally ingestible time-release substance which withstands degradation by the gastric acids of the stomach and releases the N-acetylglucosamine in the bowel.

8. A composition as claimed in claim 2 wherein the carrier is an orally ingestible time-release substance which withstands degradation by the gastric acids of the stomach and releases the N-acetylglucosamine in the bowel.

9. A composition as claimed in claim 3 wherein the foam comprises N-acetylglucosamine, a surfactant, an adjuvant and a blowing agent.

10. A composition as claimed in claim 4 wherein the foam comprises N-acetylglucosamine, a surfactant, an adjuvant and a blowing agent.

11. A composition as claimed in claim 9 wherein the carrier comprises one or more substances selected from the group consisting of propylene glycol, emulsifying wax, polyoxyethylene-10-stearyl ether, ethoxylated cetyl and stearyl alcohols, stearath-10, cetyl alcohol, methyl paraben, propyl paraben, trolamine, purified water, cetyl alcohol, ethoxylated stearyl alcohol, polyoxyethylene-10-stearyl ether, methyl and propyl parabens, propylene glycol, dry ethanol amine, de-ionized water and suitable propellents.

12. A composition as claimed in claim 10 wherein the carrier comprises one or more substances selected from the group consisting of propylene glycol, emulsifying wax, polyoxyethylene-10-stearyl ether, ethoxylated cetyl and stearyl alcohols, stearath-10, cetyl alcohol, methyl paraben, propyl paraben, trolamine, purified water, cetyl alcohol, ethoxylated stearyl alcohol, polyoxyethylene-10-stearyl ether, methyl and propyl parabens, propylene glycol, dry ethanol amine, de-ionized water and suitable propellents.

13. A composition as claimed in claim 5 wherein the suppository base is selected from the group consisting of theobroma oil, glycerinated gelatin, hydrogenated vegetable oil, polyalkyl glycol, fatty acid ester of polyalkylene glycol, coconut oil base, hydrogenated fatty acid, hydrogenated vegetable oil, monoglyceride, cocoa butter, petroleum oil, beeswax, glycerine, polyethylene glycol 600 dilaurate, hydrogenated cocoa glyceride and polyethylene glycol.

14. A composition as claimed in claim 6 wherein the suppository base is selected from the group consisting of theobroma oil, glycerinated gelatin, hydrogenated vegetable oil, polyalkyl glycol, fatty acid ester of polyalkylene glycol, coconut oil base, hydrogenated fatty acid, hydrogenated vegetable oil, monoglyceride, cocoa butter, petroleum oil, beeswax, glycerine, polyethylene glycol 600 dilaurate, hydrogenated cocoa glyceride and polyethylene glycol.

15. A composition as claimed in claim 7 wherein the time release substance is selected from the group consisting of an acrylic-based resin coating, a methacrylic acid copolymer, an acrylic-based resin mixed with a suitable non-medicinal carrier selected from the group consisting of lactose, magnesium stearate, polyethylene glycol, polyvinyl pyrolidone, or sodium starch glycolate, cellulose or ethyl cellulose, a matrix composition comprised of a hydrophilic polymer and an enteric polymer, a cellulose derivative, polyvinyl acetate phthalate, or polyvinyl acetate phthalate mixed with a plasticizer, a polysaccharide which is decomposable in the bowel, a locust bean gum or a guar gum, a film-forming polymer having hydrophilic groups, a film-forming acrylic polymer in admixture with a polysaccharide comprising from 30 to 100% by weight of at least one monomer selected from the group consisting of lower alkyl esters of acrylic acid and lower alkyl esters of methacrylic acid, a hydrocolloid gum obtained from a higher plant, and an anionic carboxylic polymer which does not dissolve at a pH below about 4 but is soluble at a pH ranging from about 4 to about 7.5.

16. A composition as claimed in claim wherein the foam comprises 0.5 to 5 grams of N-acetylglucosamine as the active ingredient and 20 g of a foam containing propylene glycol, emulsifying wax, polyoxyethylene-10-stearyl ether, cetyl alcohol, methylparaben and propylparaben, trolamine, purified water and inert propellents, dichlorodifluoromethane or dichlorotetrafluoroethane.

17. A composition as claimed in claim 7 wherein the composition comprises between about 0.1% by weight to about 90% by weight of N-acetylglucosamine, coated with about 5% by weight to about 29% by weight of a hydrophilic polymer, and from about 0.5% by weight to about 25% by weight of an acrylic polymer which dissolves at a pH in the range of about 5.0 to about 7.5.

18. A method of treating a patient suffering from inflammatory bowel disease comprising administering to the bowel of said patient a composition comprising a therapeutic amount of N-acetylglucosamine and a bowel compatible pharmacologically acceptable carrier, said composition being administered topically to the location of the inflammatory bowel disease in the bowel of the patient suffering from inflammatory bowel disease.

19. A method as claimed in claim 18 wherein the N-acetyl-glucosamine is present in an amount between about 0.5 gram and 5 grams per enema.

20. A method as claimed in claim 18 wherein the pharmacologically acceptable carrier is distilled or purified water.

21. A method as claimed in claim 19 wherein the pharmacologically acceptable carrier is distilled or purified water.

22. A method as claimed in claim 20 wherein the enema is administered to said patient by an enemator.

23. A method as claimed in claim 18 wherein the carrier is a bowel compatible foam which coats the colon.

24. A method as claimed in claim 19 wherein the carrier is a bowel compatible foam which coats the colon.

25. A method as claimed in claim 18 wherein the carrier is a suppository which is solid at room temperature but melts at body temperature.

26. A method as claimed in claim 19 wherein the carrier is a suppository which is solid at room temperature but melts at body temperature.

27. A method as claimed in claim 18 wherein the carrier is an orally ingestible time-release substance which withstands degradation by the gastric acids of the stomach and releases the N-acetylglucosamine in the bowel.

28. A method as claimed in claim 19 wherein the carrier is an orally ingestible time-release substance which withstands degradation by the gastric acids of the stomach and releases the N-acetylglucosamine in the colon.

\* \* \* \* \*